United States Patent
Blair et al.

(10) Patent No.: US 10,307,156 B1
(45) Date of Patent: Jun. 4, 2019

(54) LOW PROFILE STAPLE AND METHODS FOR USING SAME

(71) Applicant: MedShape, Inc., Atlanta, GA (US)

(72) Inventors: Jeremy Webster Blair, Atlanta, GA (US); Jack Cabell Griffis, III, Vero Beach, FL (US)

(73) Assignee: MEDSHAPE, INC., Atlanta, GA (US)

( * ) Notice: Subject to any disclaimer, the term of this patent is extended or adjusted under 35 U.S.C. 154(b) by 0 days.

(21) Appl. No.: 16/058,638

(22) Filed: Aug. 8, 2018

(51) Int. Cl.
*A61B 17/064* (2006.01)
*A61B 17/00* (2006.01)

(52) U.S. Cl.
CPC ...... *A61B 17/0642* (2013.01); *A61B 17/0644* (2013.01); *A61B 2017/00867* (2013.01)

(58) Field of Classification Search
CPC .............. A61B 17/064; A61B 17/0642; A61B 17/0644; A61B 2017/0641; A61B 2017/0645; A61B 2017/0646
USPC .............................................. 606/75; 227/902
See application file for complete search history.

(56) References Cited

U.S. PATENT DOCUMENTS

| | | | |
|---|---|---|---|
| 10,117,647 B2 | 11/2018 | Cheney | |
| 2006/0058802 A1* | 3/2006 | Kofoed | A61B 17/0642 606/75 |
| 2008/0161808 A1* | 7/2008 | Fox | A61B 17/0642 606/75 |
| 2008/0319443 A1* | 12/2008 | Focht | A61B 17/0642 606/75 |
| 2010/0063506 A1* | 3/2010 | Fox | A61B 17/0642 606/75 |
| 2013/0123863 A1* | 5/2013 | Hollis | A61B 17/0642 606/328 |
| 2013/0231667 A1* | 9/2013 | Taylor | A61B 17/8085 606/75 |
| 2013/0267956 A1* | 10/2013 | Terrill | A61B 17/0642 606/75 |
| 2014/0018809 A1* | 1/2014 | Allen | A61B 17/0642 606/75 |
| 2015/0133940 A1* | 5/2015 | Palmer | A61B 17/0642 606/75 |
| 2015/0313592 A1* | 11/2015 | Coillard-Lavirotte | A61B 17/0642 606/75 |
| 2016/0000434 A1* | 1/2016 | Cocaign | A61B 17/0642 606/75 |
| 2016/0030039 A1* | 2/2016 | Seavey | A61B 17/0682 206/210 |
| 2016/0066907 A1* | 3/2016 | Cheney | A61B 17/0684 606/75 |
| 2016/0199060 A1* | 7/2016 | Morgan | A61B 17/068 227/175.1 |

* cited by examiner

*Primary Examiner* — Eric S Gibson
(74) *Attorney, Agent, or Firm* — Morris, Manning & Martin, LLP; Bryan D. Stewart; Daniel T. Begasse

(57) ABSTRACT

According to particular embodiments, the present staple includes a low-profile bridge and has the capacity for high sustained compression. In some embodiments, the staple includes a bridge with a continuous cross-section, legs with teeth cut therein (e.g., opposed to protruding from, as discussed herein), and legs including an angle of about 24 degrees.

20 Claims, 22 Drawing Sheets

LOW PROFILE STAPLE AND METHODS FOR USING SAME

BACKGROUND

Generally, surgical staples are used in some orthopedic indications for holding two bone segments together. Typically, segments of the same bone are separated (e.g., broken, fractured, etc.) and legs of a staple are inserted into each bone segment to compress ends of two (or more) segments of a broken bone together to promote healing of the bone (e.g., such that the bone segments heal back together).

As will be understood, staples can compress bone segments together based on stored strain profiles of the staples. At minimum, such compression can limit the distance between broken bone segments, thereby possibly helping reduce bone healing time by eliminating gaps that need to be filled by the bones/body when healing. Further, such compression may help increase/speed bone growth.

As will also be understood, space within a body is limited and lower profile staples are desirable. However, in creating a low-profile staple (e.g., a staple that has minimum rise above the surface of a bone when the staple is fully inserted), the amount of stored strain (e.g., amount of compression the staple can impart when inserted) may be limited do to certain design constraints. Further, such low-profile staples may include localized strain concentrations (at corners and the like), which may increase risk of fatigue failure.

Therefore, there exists a need for a low profile surgical staple and has the capacity for high sustained compression and that minimizes localized strain concentrations.

BRIEF SUMMARY OF THE DISCLOSURE

Briefly described, and according to one embodiment, aspects of the present disclosure generally relate to an improved low profile staple with high sustained compression and improved fatigue performance (e.g., minimized localized strain concentrations).

According to particular embodiments, a staple includes: A) a bridge with a substantially continuous cross-section along at least 80% of a length of the bridge, a substantially smooth top surface, and a width that is greater than a thickness of the bridge; and B) one or more legs integrally formed with the bridge, each of the one or more legs forming an angle of greater than approximately 20 degrees with at least one other leg of the one or more legs. In some embodiments, the staple described above (or anywhere else herein), wherein: A) each of the one or more legs includes a proximal end and a distal end and each distal end includes a wedge-shaped tip; B) each of the one or more legs includes an inner surface and a plurality of teeth, wherein each of the plurality of teeth are cut out of a respective leg such that a point of each tooth lies substantially in the same plane as the inner surface of the respective leg; C) a midpoint of each of the one or more legs is located approximately at a midpoint of the width of the bridge; D) the staple includes at least one radius for transitioning from an outer edge of the bridge to a surface of a particular leg of the one or more legs; E) the staple includes a sloping portion from the substantially smooth top surface of the bridge to an outer surface of at least one of the one or more legs; F) each of a first subset of the plurality of teeth of a first leg of the one or more legs includes a first angle; G) each of s second subset of the plurality of teeth of the first leg includes a second angle, wherein the second angle is less than the first angle; H) the staple includes nitinol; I) the length of the bridge is at least 8.00 mm; J) a radius of the length of the bridge is at least 11.00 mm; K) the length of the bridge is at least 18.00 mm; and/or L) the radius of the length of the bridge is at least 31.00 mm.

According to a first aspect, a method of using a surgical staple includes: A) deforming a staple from a first position to a second position for inserting the staple into tissue of a patient, wherein: 1) the staple includes: a) a bridge with a substantially continuous cross-section along at least 80% of a length of the bridge, a smooth top surface, and a width that is greater than a thickness of the bridge; and b) one or more legs integrally formed with the bridge; 2) in the first position, each of the one or more legs form an angle of greater than approximately 20 degrees with at least one other leg of the one or more legs; 3) in the second position, each of the one or more legs are substantially parallel with the at least one other leg of the one or more legs and strain is distributed substantially evenly throughout the bridge; and 4) the staple, when inserted into the tissue of the patient exerts compressive force on the tissue of the patient. In some aspects, the method described above (or elsewhere herein), wherein: A) each of the one or more legs includes a proximal end and a distal end and each distal end includes a wedge-shaped tip; B) each of the one or more legs including an inner surface and a plurality of teeth; C) each of the plurality of teeth are cut out of a respective leg such that a point of each tooth lies substantially in the same plane as the inner surface of the respective leg; D) a midpoint of each of the one or more legs is located approximately at a midpoint of the width of the bridge; E) the staple includes at least one radius for transitioning from an outer edge of the bridge to a surface of a particular leg of the one or more legs; F) the staple includes a sloping portion from the smooth top surface of the bridge to an outer surface of at least one of the one or more legs; G) each of a first subset of the plurality of teeth of a first leg of the one or more legs includes a first angle; H) each of a second subset of the plurality of teeth of the first leg includes a second angle, wherein the second angle is less than the first angle; I) the staple includes nitinol; J) the length of the bridge is at least 8.00 mm; K) a radius of the length of the bridge is at least 11.00 mm; L) the length of the bridge is at least 18.00 mm; and/or I) the radius of the length of the bridge is at least 31.00 mm.

These and other aspects, features, and benefits of the claimed invention(s) will become apparent from the following detailed written description of the disclosed embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
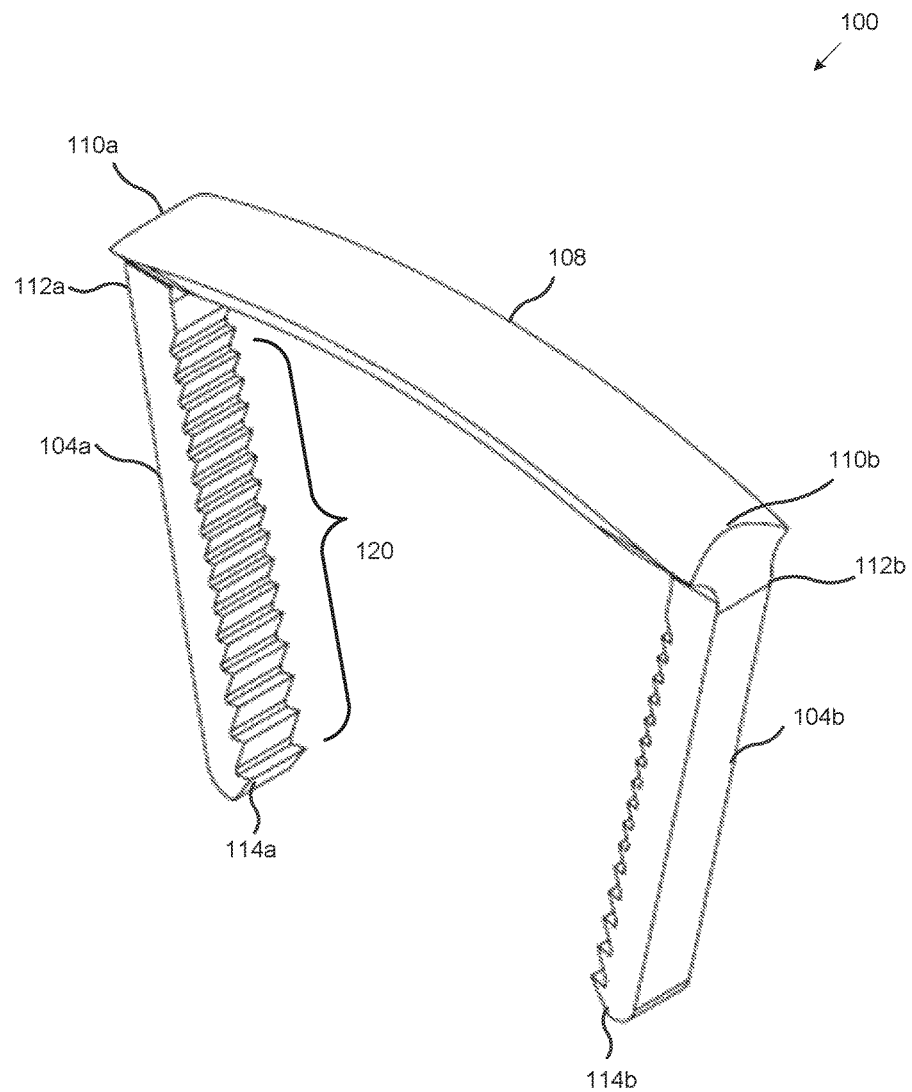
FIG. 1 illustrates a perspective view of a staple, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

According to particular embodiments, the present staple includes a low-profile bridge that has the capacity for high sustained compression and improved fatigue performance (e.g., minimized localized strain concentrations). In some embodiments, the staple includes a bridge with a continuous cross-section, legs with teeth cut therein (e.g., opposed to protruding from, as discussed herein), and legs with an angle of about 24 degrees (e.g., 12 degrees from vertical).

Some existing staples may include bridges with a discontinuous cross-section, which may limit the arch/radius of the bridge and likewise limit the angle at which the legs are positioned. As will be understood, the amount of compression a staple can impart on bone segments is related to the arch/radius of the bridge and angle in which the legs are positioned. In general, the greater the angle of the legs from vertical, the greater sustained compression the staple can impart on bone segments.

For example, a particular bone staple is manufactured with an arched bridge of a particular radius and legs of a particular angle from vertical. Continuing with this example, for insertion into one or more bone segments, the staple is deformed such that the bridge is substantially flattened/straightened from its resting arched position and the legs are substantially parallel/perpendicular to the substantially flattened bridge (e.g., the legs are at 0 degrees from vertical or are vertical). In this position, in this example, the staple stores strain as the bridge and legs attempt to return to their original position. As will be understood, the amount of stored strain is related to the arch/radius of the bridge and the angle of the legs. Therefore, the greater the arch/radius of the bridge and the greater the angle of the legs, the more stored strain in the staple and the more potential sustained compression force the staple can impart on bone segments upon insertion.

As will be recognized by one of ordinary skill in the art, the staples disclosed herein have a number of advantages over previously designed staples. First, various embodiments of the staples disclosed herein have a bridge with a continuous, low profile cross-section. Such a cross-section enables the bridge to have more stored strain and minimized localized strain than a bridge with a discontinuous cross-section (e.g., facets, different cross-sections in various portions of the bridge, etc.).

Second, some embodiments of the staples disclosed herein include teeth that are cut out of the legs (opposed to protruding therefrom). In these embodiments (and others), the legs may be wider/thicker than other staples, but have a similar structure for the teeth. As will be understood, wider/thicker legs may result in increased stiffness as compared to staples with less wide/thick legs. As will also be understood, stiff legs (along with a constant-cross section bridge) may help distribute stored strain of a particular staple substantially evenly along the bridge portion, minimizing or eliminating stress concentrations at the interface of the legs and bridge (or at corners or surface features of a non-continuous cross-section bridge).

Third, a combination of the above elements and advantages may result in a staple that is lower profile (along the entire bridge), has higher sustained compression (and higher compression force on a patient's tissue) for longer periods of time (compared to other staples), and a staple that has high durability (lower fatigue failure/improved fatigue performance) than other staples.

As will be understood, the exemplary staples discussed herein may be manufactured from any suitable material, including, but not limited to stainless steel, titanium, nitinol, biocompatible materials, and/or combinations of any of the previously mentioned materials.

Various aspects of the instant staple will be discussed in the following sections.

Exemplary Staple

Referring now to the figures, for the purposes of example and explanation of the fundamental processes and components of the disclosed staple, reference is made to FIG. 1, which illustrates an exemplary staple 100, according to one embodiment of the present disclosure. In various embodiments, the staple 100 includes a bridge 108 and two legs (104a, 104b). The staple 100 size (bridge×leg length) may be greater than, less than or equal to about 8 mm×8 mm, 10 mm×10 mm, 12 mm×12 mm, 14 mm×14 mm, 18 mm×18 mm, 18 mm×20 mm, 20 mm×18 mm, 20 mm×22 mm, or 26 mm×20 mm.

Figure 8:
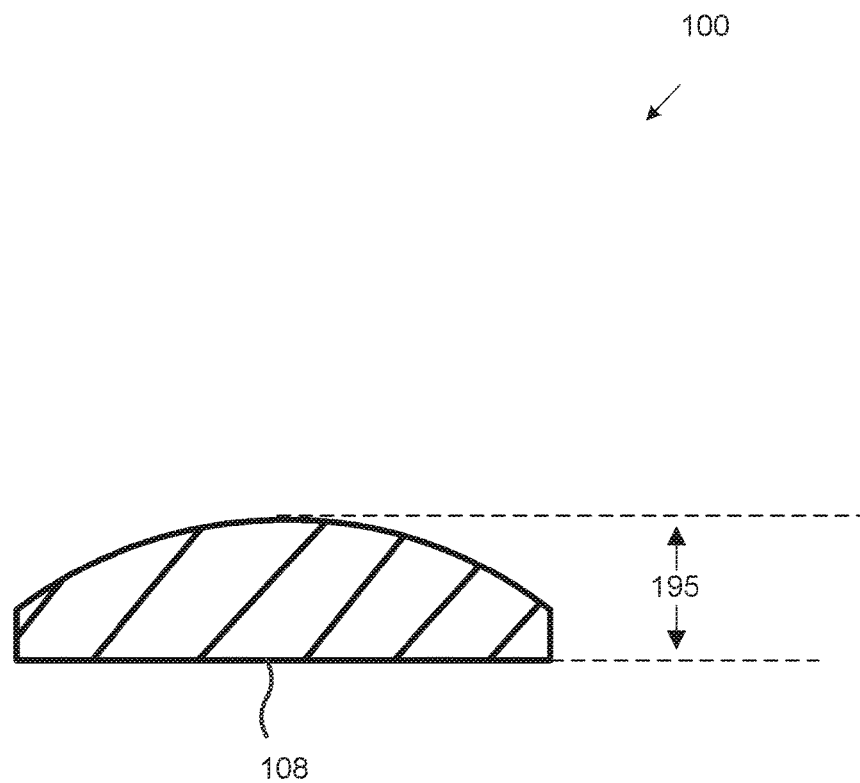
FIG. 8 illustrates a cross sectional view of the bridge shown in FIG. 7, according to one embodiment of the present disclosure.
Figure 9:
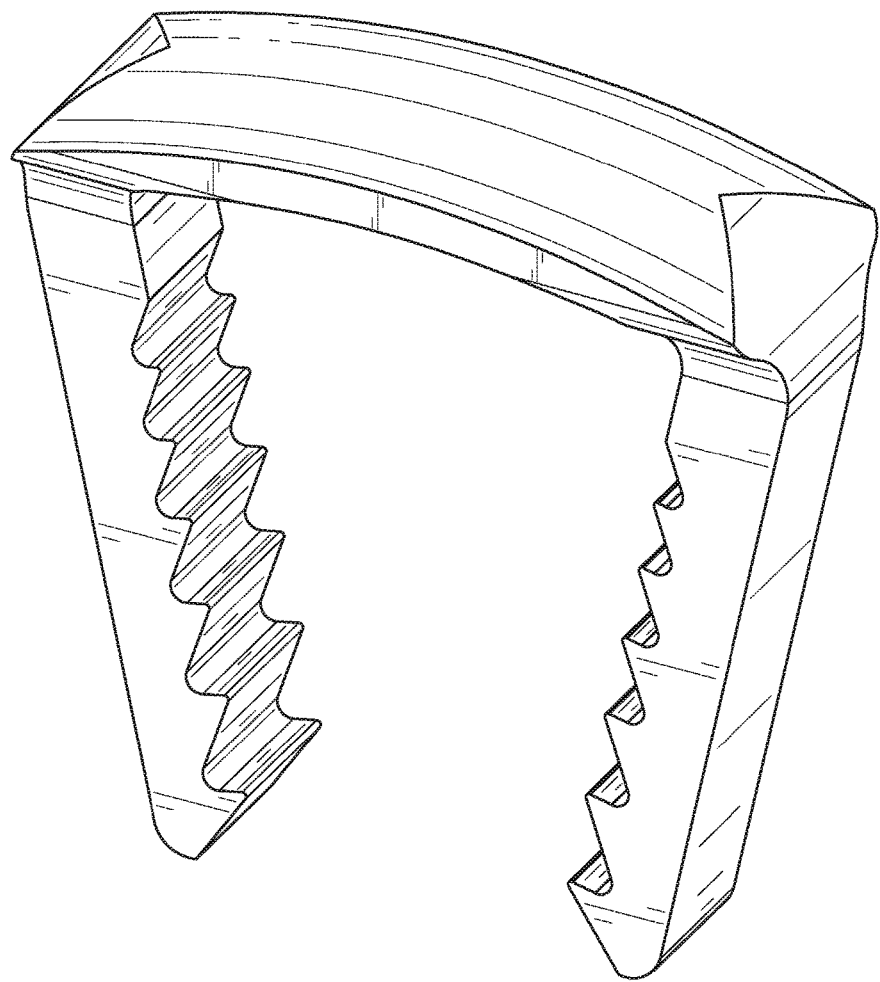
FIG. 9 is a perspective view of an exemplary low profile staple, according to one embodiment of the present disclosure.
Figure 10:
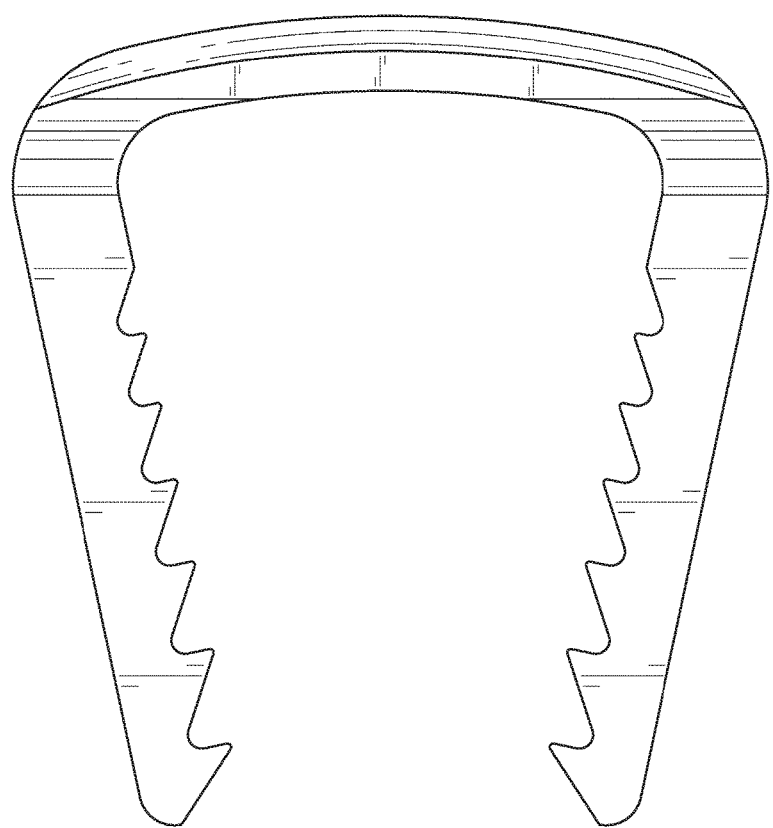
FIG. 10 is a front view of an exemplary low profile staple, according to one embodiment of the present disclosure.
Figure 11:
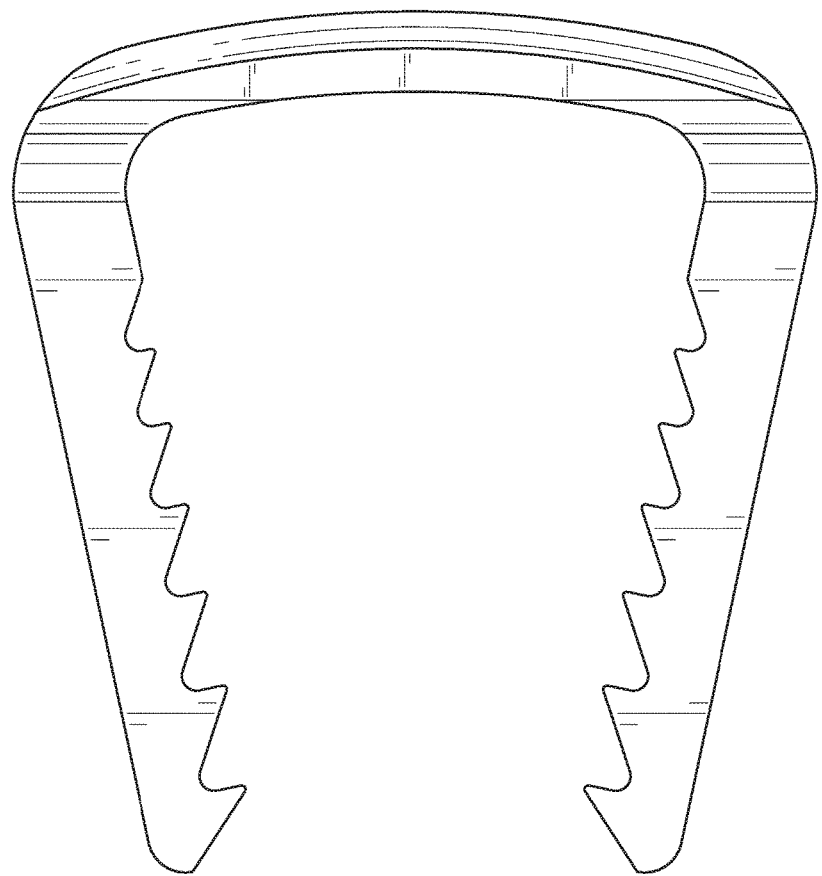
FIG. 11 is a back view of an exemplary low profile staple, according to one embodiment of the present disclosure.
Figure 12:
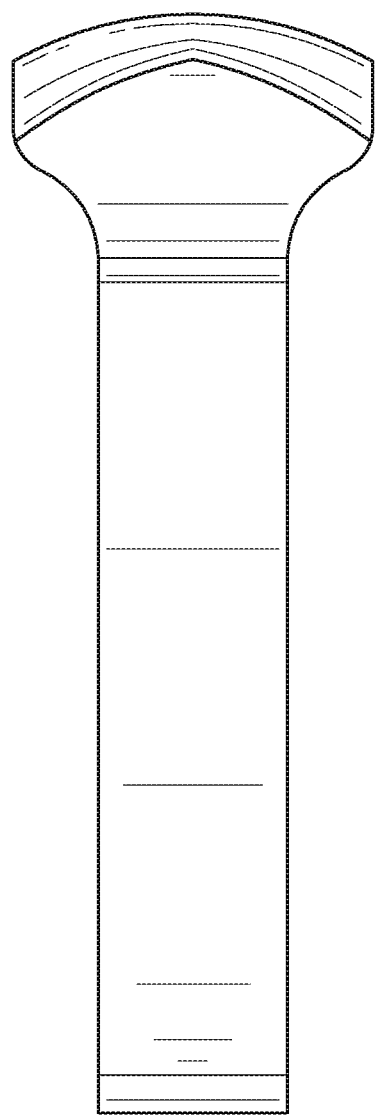
FIG. 12 is a side view of an exemplary low profile staple, according to one embodiment of the present disclosure.
Figure 13:
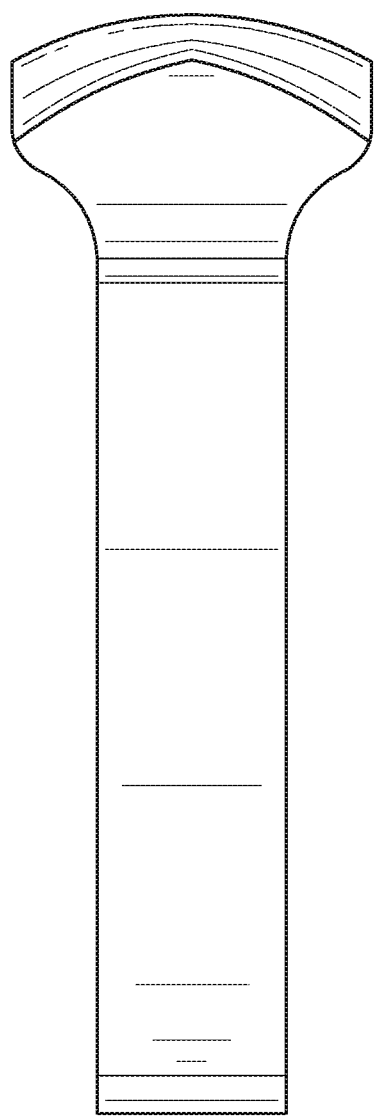
FIG. 13 is a side view of an exemplary low profile staple, according to one embodiment of the present disclosure.
Figure 14:
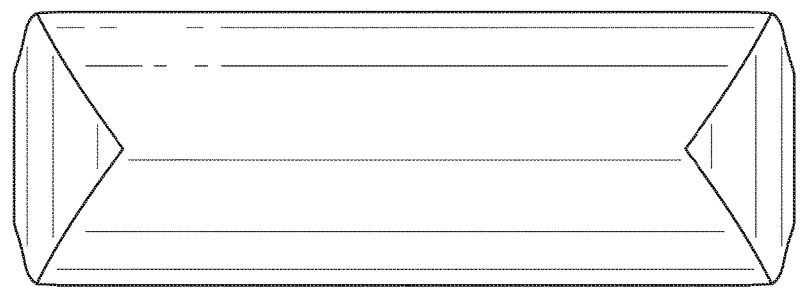
FIG. 14 is a top view of an exemplary low profile staple, according to one embodiment of the present disclosure.
Figure 15:
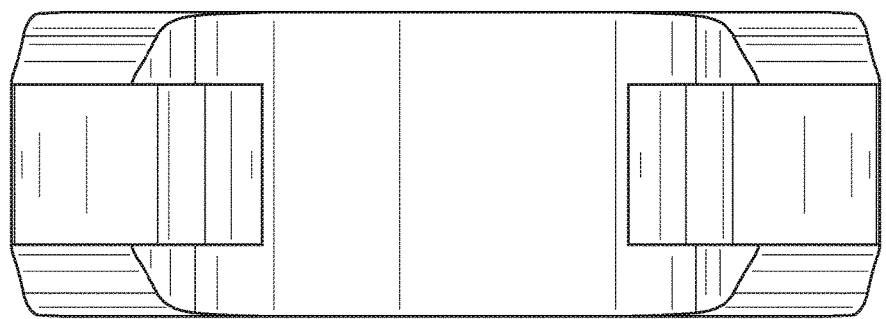
FIG. 15 is a bottom view of an exemplary low profile staple, according to one embodiment of the present disclosure.
Figure 16:
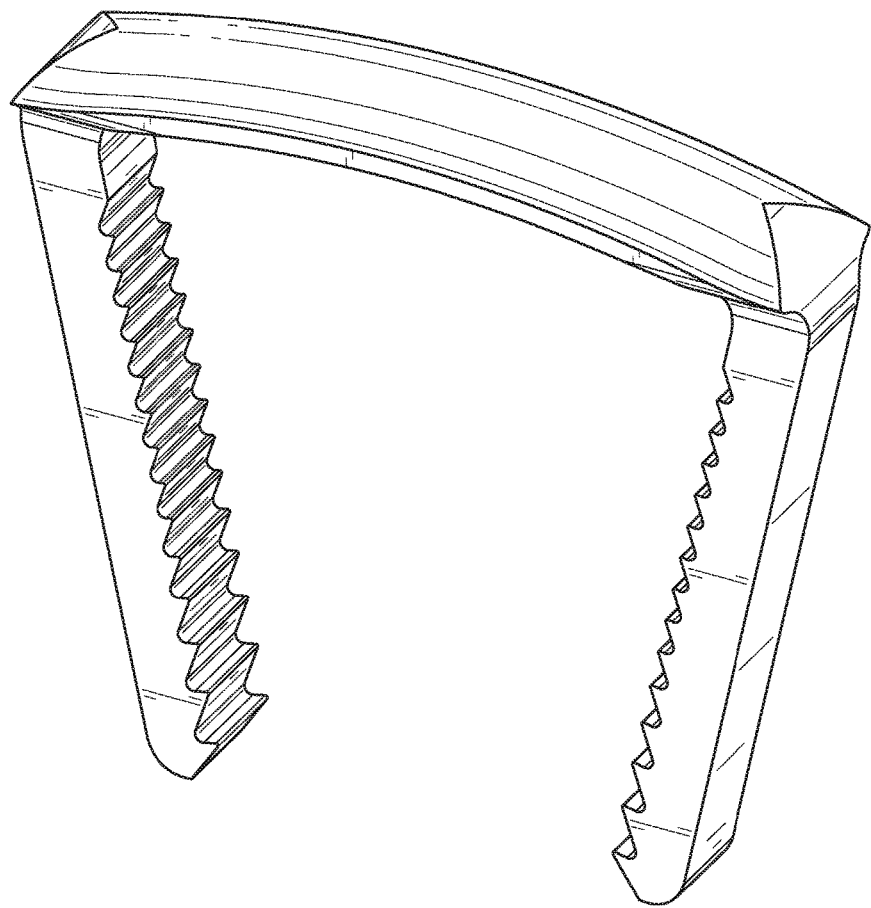
FIG. 16 is a perspective view of an exemplary low profile staple, according to one embodiment of the present disclosure.
Figure 17:
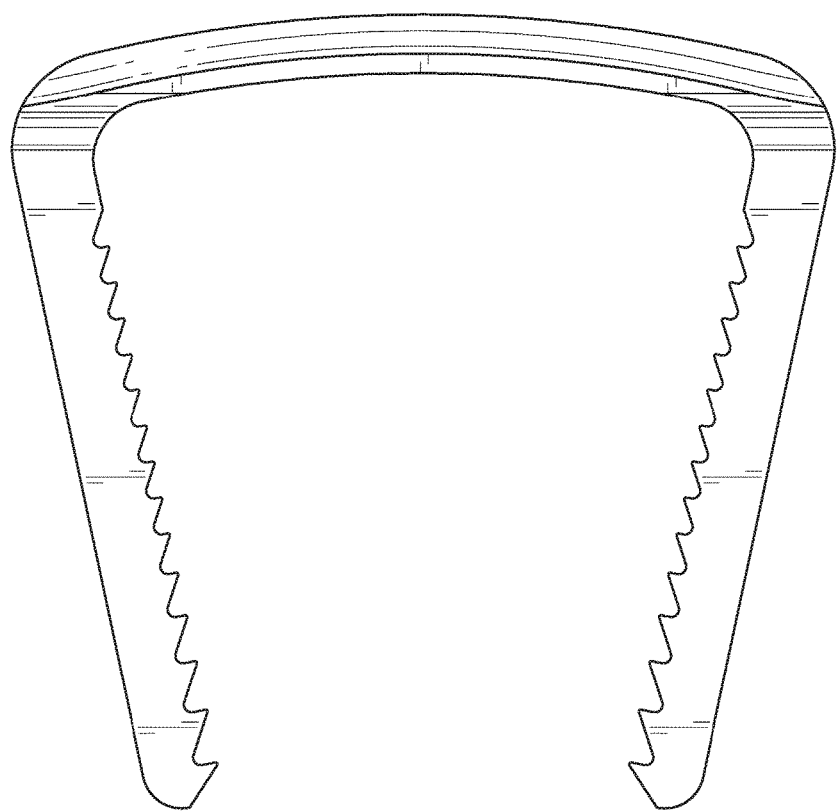
FIG. 17 is a front view of an exemplary low profile staple, according to one embodiment of the present disclosure.
Figure 18:
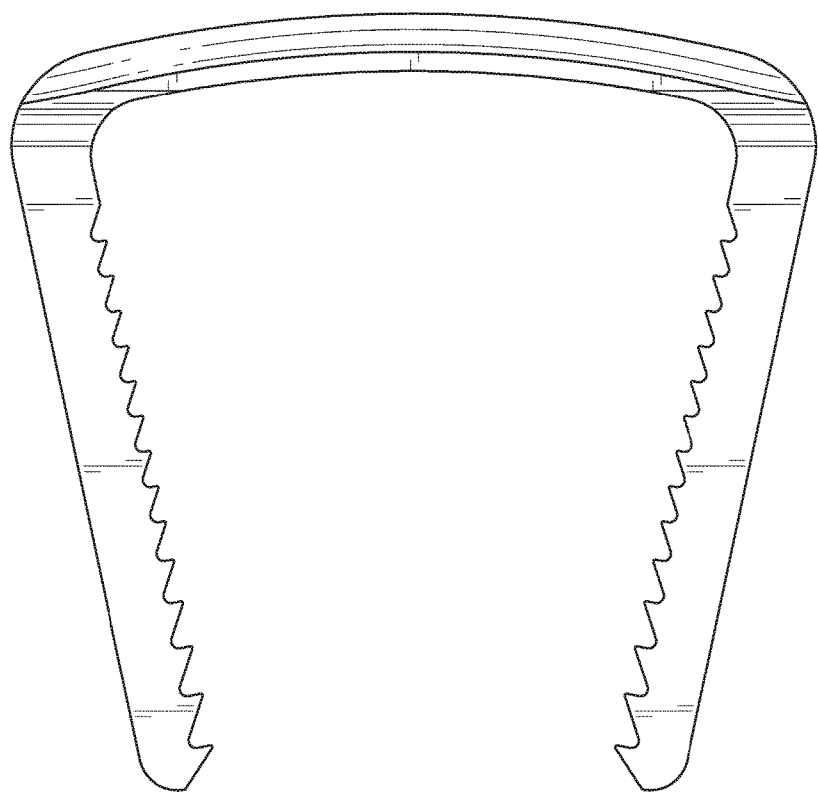
FIG. 18 is a back view of an exemplary low profile staple, according to one embodiment of the present disclosure.
Figure 19:
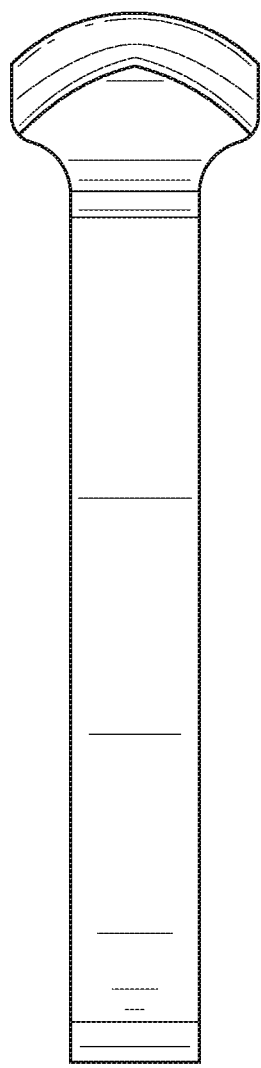
FIG. 19 is a side view of an exemplary low profile staple, according to one embodiment of the present disclosure.
Figure 20:
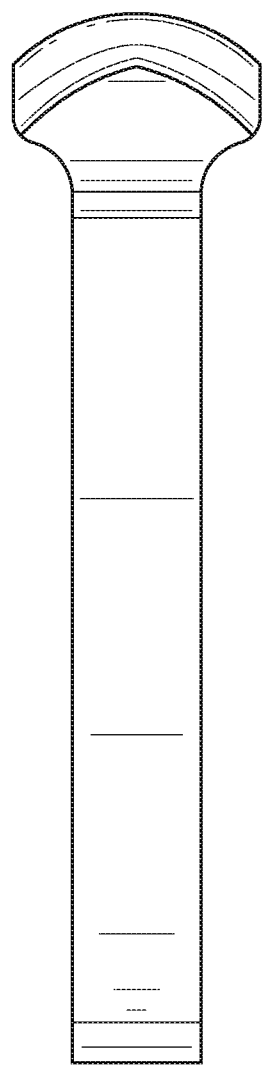
FIG. 20 is a side view of an exemplary low profile staple, according to one embodiment of the present disclosure.
Figure 21:
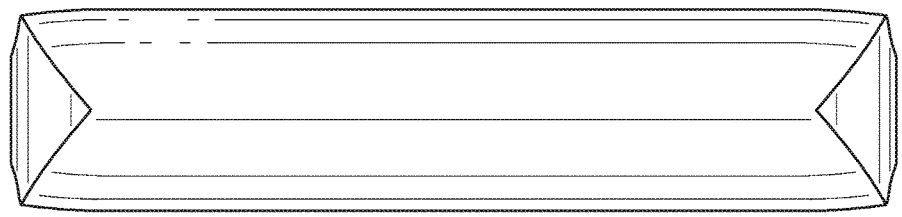
FIG. 21 is a top view of an exemplary low profile staple, according to one embodiment of the present disclosure.
Figure 22:
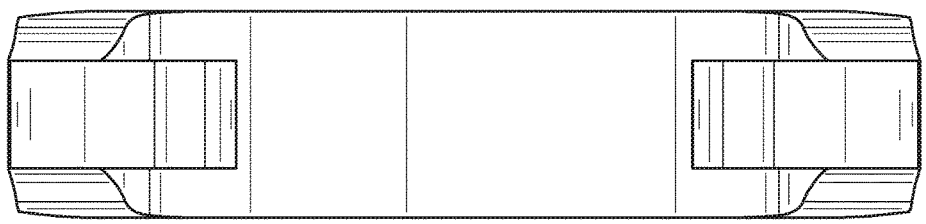
FIG. 22 is a bottom view of an exemplary low profile staple, according to one embodiment of the present disclosure.

In particular embodiments, the bridge 108 has a first end 110a and a second end 110b and includes a substantially constant cross-section between the first end 110a and the second end 110b (as further discussed in relation to FIG. 8). In at least one embodiment, the bridge 108 is substantially smooth across a top surface (e.g., between ends 110a and 110b). In some embodiments, the bridge 108 includes one or more particular radii, which will be further discussed regarding FIG. 5.

In various embodiments, the staple 100 includes legs 104a and 104b that are integrally formed with the bridge 108. In some embodiments, the legs 104a and 104b may be generally straight from a proximal end (112a, 112b) to a distal end (114a, 114b) and may have a generally rectangular cross-section. In some embodiments, the legs (104a, 104b) may have any suitable shape (e.g. generally cylindrical, serpentine, obround, oval, tubular, etc.).

As shown in the embodiment of FIG. 1, each of the legs 104a and 104b include a distal end (114a, 114b). As shown, each of the distal ends 114a and 114b are formed into a wedge-like shape for easier insertion of a staple leg into tissue (e.g., bone). The distal ends 114a and 114b may form any suitable shape (e.g., points, rounded edges, blocked edges, etc.).

In various embodiments, the staple 100 may have a plurality of teeth 120 cut into the legs 104a and 104b. In some embodiments, the teeth 120 may be located on the internal face of the legs (104a, 104b). In various embodiments, the teeth 120 may extend along the entire length of the legs 104a and 104b. In some embodiments, the teeth 120 may extend along a partial length of the legs 104a and 104b. In various embodiments, the teeth 120 may be wedge-shaped, curved, straight or any combination thereof. As will be understood, a staple may include two or more legs (e.g., three, four, etc.) and each leg may have a different (or the same) number of teeth. In further embodiments, each staple leg may have different sized or shaped teeth (e.g., a staple with four legs may include teeth of a first shape along an inner pair of legs and teeth of a second shape long an outer pair of legs).

Figure 2:
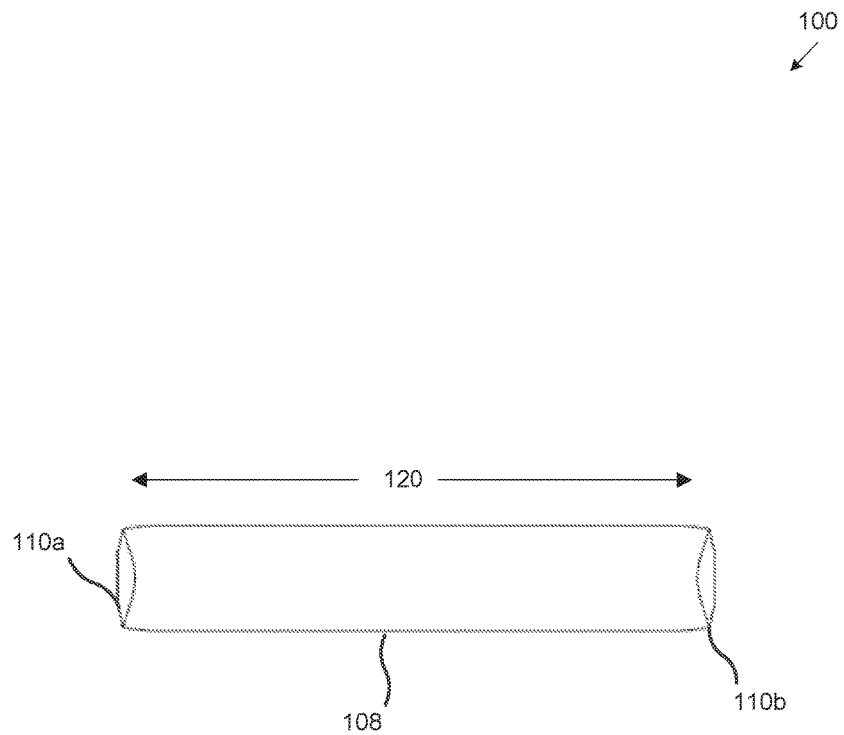
FIG. 2 illustrates a top view of a staple, according to one embodiment of the present disclosure.

FIG. 2 is a top view of a staple, according to one embodiment of the present disclosure. In various embodiments, the top of the staple 100 includes the bridge 108, which may be curved between two ends 110a and 110b (curvature not shown in FIG. 2), with a smooth top surface and low profile cross-section that is substantially constant throughout the entire bridge 108.

In some embodiments, the bridge 108 includes a length 120 that may be greater than, less than or equal to about 8 mm to 35 mm. In particular embodiments, the bridge 108 has a length 120 that may be greater than, less than or equal to about 8.82 mm, 10.82 mm, 12.82 mm, 14.83 mm, 19.11 mm, 21.11 mm, or 27.12 mm.

Figure 3:
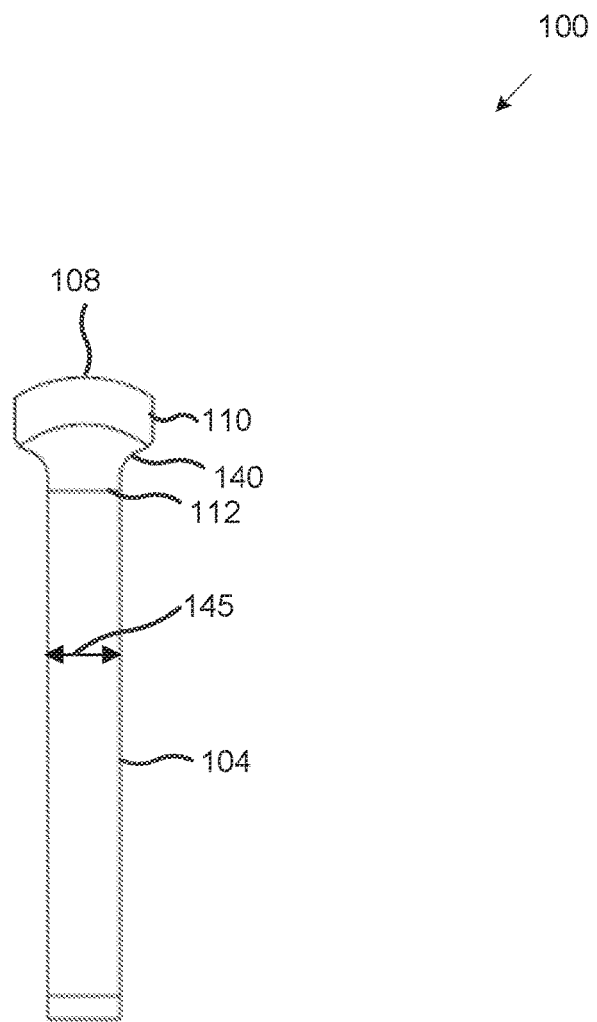
FIG. 3 illustrates a side view of a staple, according to one embodiment of the present disclosure.

FIG. 3 is a side view of a staple, according to one embodiment of the present disclosure. In the embodiment shown, the staple 100 includes a bridge 108 having an end 110 and a leg 104. In various embodiments, the bridge 108 is smooth and with a low-profile geometry that enables more curvature of the bridge, which may create greater sustained compression when the staple is inserted into tissue (as further discussed herein). In some embodiments, the top and bottom portion of the bridge 108 is generally arched in shape.

In various embodiments, the staple 100 may have a leg 104 connected to the bottom portion of bridge 108 near the proximal end 112 of the leg 104. In some embodiments, there is a transitional area that is sloped from the proximal end 112 of the leg 104 to the bridge 108. In some embodiments, this transitional area may have a radius that may be greater than, less than, or equal to about 1.00 mm. In at least one embodiment, the staple includes a shoulder 140 that transitions from the width of the bridge 108 to the depth 145 of the leg 104.

In some embodiments, the shoulder 140 may have one or more radii that may be greater than, less than, or equal to about 0.50 mm to 1.50 mm. In particular embodiments, the shoulder 140 has one or more radii that may be greater than, less than, or equal to about 0.50 mm, 1.00 mm, 1.50 mm, 2.00 mm, or 2.50 mm.

In some embodiments, the leg 104 may have a depth 145 that may be greater than, less than, or equal to about 1.00 mm to 3.00 mm. In particular embodiments, the leg 104 has a depth 145 that may be greater than, less than, or equal to about 1.5 mm, 2 mm, 2.5 mm, etc.

Figure 4:
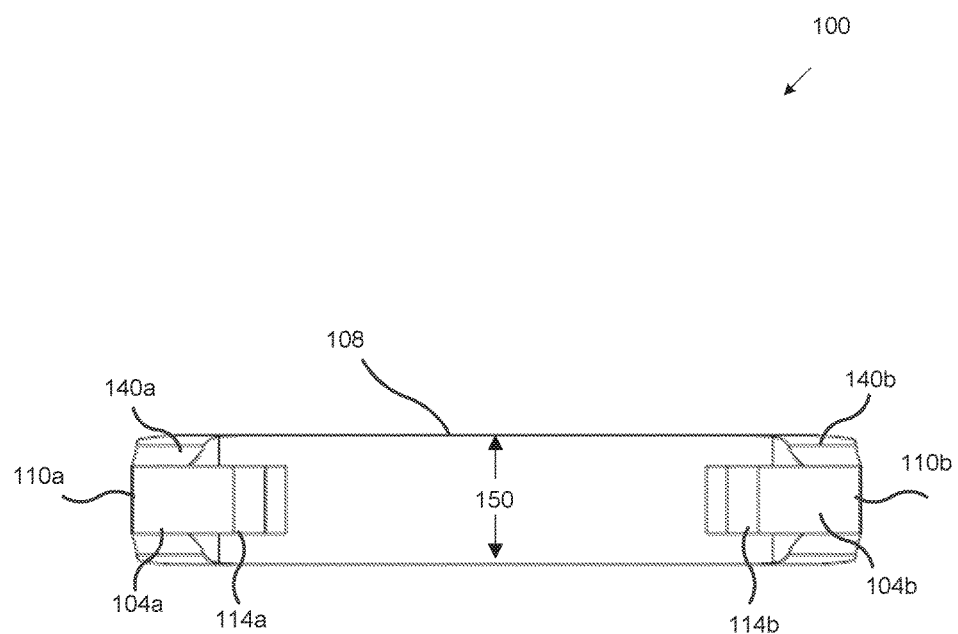
FIG. 4 illustrates a bottom view of a staple, according to one embodiment of the present disclosure.

FIG. 4 is a bottom view of a staple, according to one embodiment of the present disclosure. As depicted, the staple 100 includes a bridge 108 having two ends (110a, 110b) and legs (104a, 104b).

In various embodiments, the staple 100 includes a first shoulder 140a and a second shoulder 140b. As shown, the width of the bridge 150 is greater than a depth of the legs 104a and 104b (as described in relation to FIG. 3). As such, the first shoulder 140a and second shoulder 140b transition from the width of the bridge 150 to the depth of the legs 104a and 104b.

In some embodiments, midpoints of the legs 104a and 104b are located at a midpoint of the bridge 108 (e.g., the legs are positioned along a centerline of the bridge). In these embodiments (and others), the shoulders 140a and 140b include a slope, arch, or other transition from each edge of the bridge 108 to an edge of each of the legs 104a and 104b. In particular embodiments, the transition from the width of the bridge 108 to the depth of the legs 104a and 104b is substantially gradual and constant (e.g., a gradual slope or a constant radius arch). In some embodiments, the slope includes more than one slope of varying pitch or multiple arches of varying radii.

In some embodiments, the bridge 108 includes a width 150 that may be greater than, less than, or equal to about 1.00 mm to 5.00 mm. In particular embodiments, the bridge 108 has a width 150 that may be greater than, less than, or equal to about 3.80 mm and/or 4.80 mm.

Figure 5:
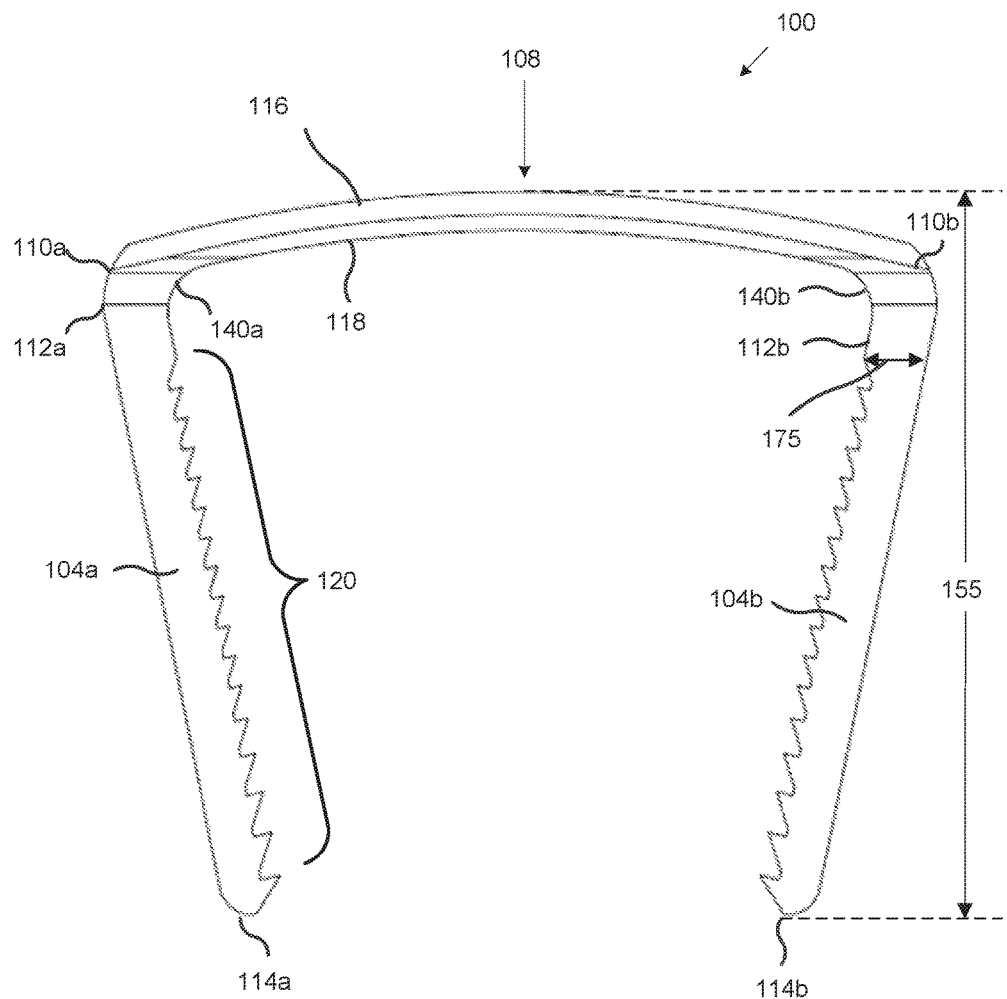
FIG. 5 illustrates a front view of a staple, according to one embodiment of the present disclosure.

FIG. 5 is a front view of a staple, according to one embodiment of the present disclosure. In various embodiments, the staple 100 may have a bridge component 108 having two ends (110a, 110b) and legs (104a, 104b).

As discussed herein, according to particular embodiments, the bridge 108 is smooth with a constant radius across a top surface of the entire bridge (e.g., between ends 110a and 110b). As shown in FIG. 5, the bridge 108 includes a top radius 116 and a bottom radius 118, with a transition between the two.

In some embodiments, the bridge 108 may have a top radius 116 that may be greater than, less than, or equal to about 8.00 mm to 60.00 mm. In particular embodiments, the bridge 108 has a top radius 116 that may be greater than, less than, or equal to about 11.24 mm, 16.06 mm, 20.88 mm, 25.69 mm, 31.75 mm, 36.56 mm, and/or 51.01 mm.

According to at least one embodiment, the bridge 108 may have a bottom radius 118 that may be greater than, less than, or equal to a range from about 8.00 mm to 60.00 mm. In particular embodiments, the bridge 108 may have a bottom radius 118 that may be greater than, less than, or equal to about 10.24 mm, 14.98 mm, 19.71 mm, 24.44 mm, 30.33 mm, 35.06 mm, and/or 49.26 mm.

In some embodiments, the curvature of the bridge (along with other features) may help distribute strain substantially equally long the length of the bridge. In at least one embodiment, the curvature of the bridge may help distribute strain equally between the legs (104a, 104b), shoulders (140a, 140b) and the bridge 108.

In various embodiments, the bridge 108 first end 110a includes a first shoulder 140a and the second end 110b includes a second shoulder 140b.

In various embodiments, the staple 100 legs (104a, 104b) extend downward from the bridge 108 and have smooth outer surfaces with a plurality of teeth 120 found in the inner surfaces. In various embodiments, each leg has a proximal (112a, 112b) and distal end, wherein the distal ends (114a, 114b) include bone penetrating features.

In one embodiment, the legs 104a and 104b have a particular length 155 as measured from the bottom of leg to the top of the bridge 108. In the embodiment shown, the legs 104a and 104b have substantially the same length. In some embodiments, legs 104a and 104b may have different lengths, depending on the application of the staple 100.

In some embodiments, the legs (104a, 104b) may have a length 155 greater than, less than, or equal to about 9.00 mm to 24.00 mm. In particular embodiments, the legs (104a, 104b) have a length greater than, less than, or equal to about 9.48 mm, 11.62 mm, 13.77 mm, 15.90 mm, 20.23 mm, 20.41 mm, 22.19 mm, 22.33 mm, or 24.93 mm.

In one or more embodiments, the legs (104a, 104b) may have a width 175 that may be greater than, less than, or equal to 1.00 mm to 3.00 mm. In particular embodiments, the legs (104a, 104b) have a width 175 that may be greater than, less than, or equal to 1.50 mm or 2.00 mm.

Figure 6:
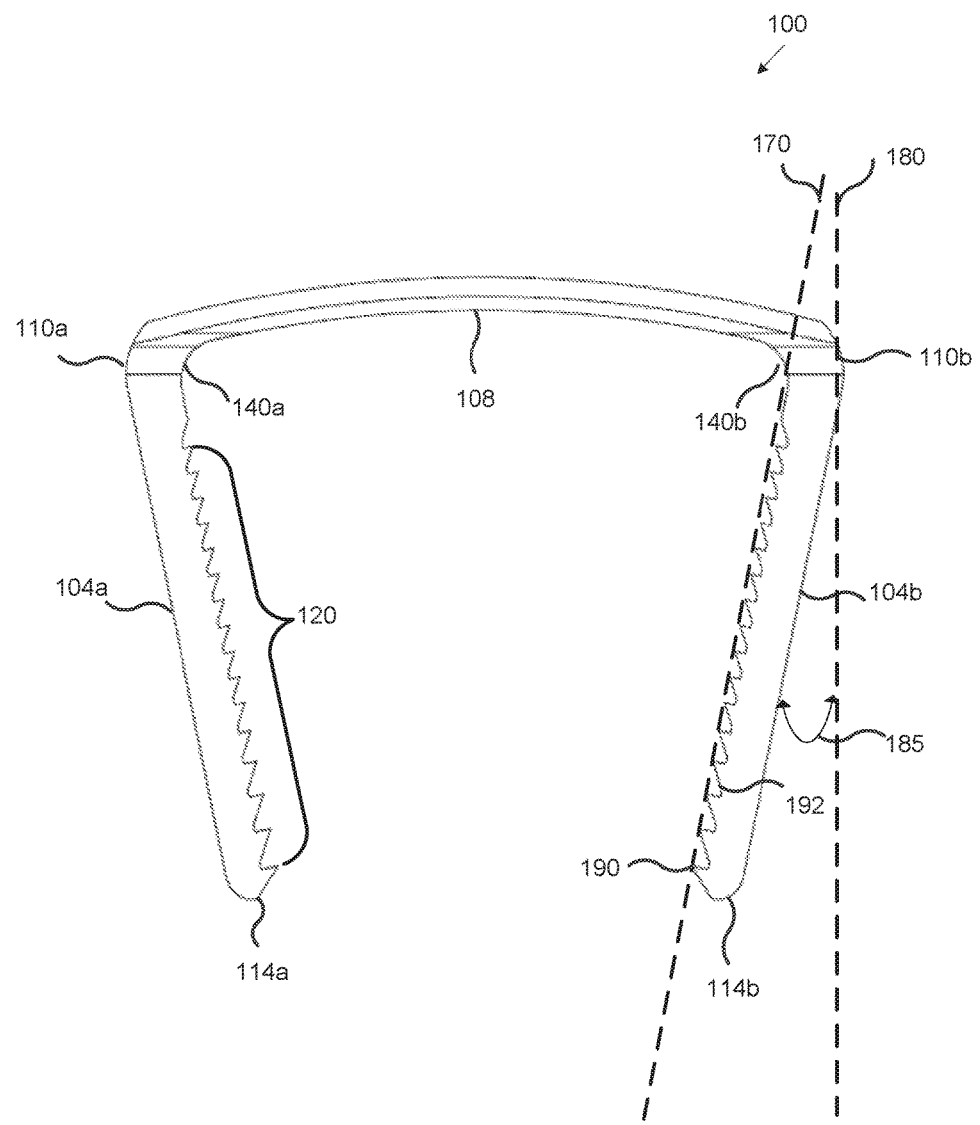
FIG. 6 illustrates a front view of a staple, according to one embodiment of the present disclosure.

Turning now to FIG. 6, a front view of a staple is shown, according to one embodiment of the present disclosure. Reference lines 170 and 180 are shown in FIG. 6 to help explain how the teeth 120 are created and the angle of the leg 104b from vertical, respectively.

According to at least one embodiment, the teeth 120 are cut into the legs (104a, 104b). Stated another way, in a particular embodiment, the ends (e.g., sharpest points) of the teeth 120 lie in the same plane as an inner surface of a leg. The plane of the inner surface of leg 104b is shown approximately as reference line 170. In some embodiments, the legs (104a, 104b) of staple 100 may have a various number of teeth 120 that may be greater than, less than, or equal to about 4, 6, 8, 10, 14, 16, or 18. The number of teeth included in the staple 100 may depend on the length of the legs of the staple 100 (e.g., a staple with longer legs may have more teeth).

In at least one embodiment, for the set of teeth 120, generally all of the teeth may be at 60 degrees. In particular embodiments, a tooth at the distal end of the legs is at an angle other than 60 degrees, such as for example, tooth 190 is at 45 degrees. In further embodiments, each tooth or a subset of teeth 120 may include any suitable angle or angles, including but not limited to about 20 to 85 degrees.

In some embodiments, each of the teeth 120 may have a depth 192 that may be greater than, less than, or equal to about 0.01 to 1.00 mm, 0.36 mm, 0.41 mm, 0.46 mm, 0.51 mm, 0.56 mm, or 0.58 mm.

As will be understood from discussions herein, all of the teeth 120 of the staple 100 may be substantially the same shape, depth, etc. In particular embodiments, the number of teeth, the size and depth of the teeth, etc. may vary along the length of the leg. In one embodiment, a leg may include a number of teeth near a distal end of a first depth and a number of teeth near a proximal end of a second depth, where the second depth is less than the first depth. In this embodiment (and others), the staple has larger teeth at the bottom of the staple and smaller teeth near the bridge of the staple.

In various embodiments, the legs (104a, 104b) are at an acute angle 185 of about 12 degrees from vertical (e.g., the angle between the legs is about 24 degrees), as indicated by reference line 180. In particular embodiments, the acute angle 185 may be any suitable angle within a range of about 10 to 15 degrees (e.g., the angle between the legs may be greater than 20 degrees). As will be understood from discussions herein, the angle of the legs 185 from vertical may be, in at least one embodiment, substantially similar to an angle measured from a horizontal line from the highest point on the bridge 108 (horizontal line not shown) to the end of the bridge 110a or 110b.

Figure 7:
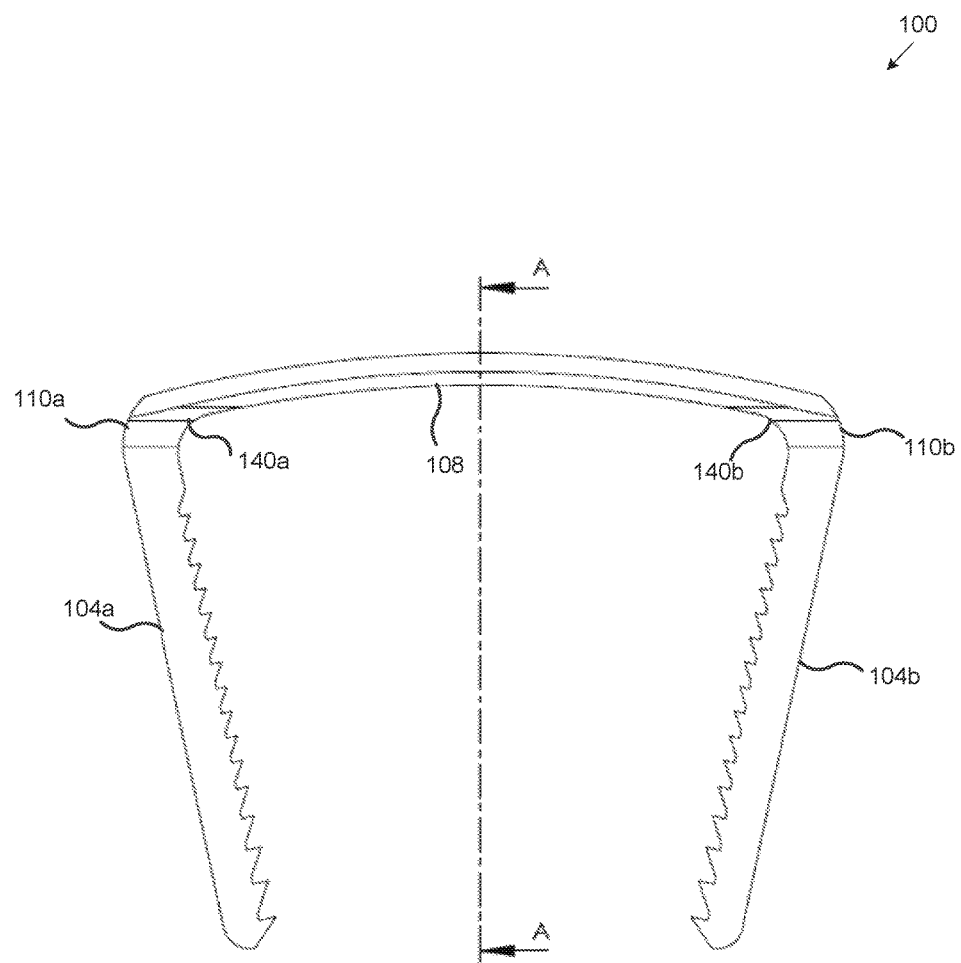
FIG. 7 illustrates a front view of a staple, according to one embodiment of the present disclosure.

FIG. 7 is a front view of a staple 100, according to one embodiment of the present disclosure. FIG. 7 shows a section line, A-A, which indicates a cross-section of the bridge 108. As shown, the section line A-A passes through an approximate midpoint of the bridge 108. As further discussed herein, the bridge 108, in particular embodiments, includes a constant cross-section. As such, although the section line A-A passes through a midpoint of the bridge 108, it should be understood that this cross section represents any cross section of the bridge 108. The cross-section will be further discussed below in relation to FIG. 8.

FIG. 8 is a cross sectional view of the bridge 108 as indicated by section line A-A shown in FIG. 7, according to one embodiment of the present disclosure. As depicted, the staple 100 includes a low-profile bridge 108. In various embodiments, the bridge 108 includes a continuous radius with a smooth top surface. In at least one embodiment, the radius of the bridge cross section top surface is about 3.00-4.00 mm. In a particular embodiment, the radius of the bridge cross section top surface is about 3.38 mm or 3.86 mm.

As shown in FIG. 8, the bridge 108 includes a particular thickness 195. In some embodiments, the bridge 108 includes a thickness 195 that may be greater than, less than, or equal to about 1.00 mm to 3.00 mm. In particular embodiments, the bridge 108 has a thickness 195 that may be greater than, less than, or equal to about 1.02 mm, 1.10 mm, 1.19 mm, 1.27 mm, 1.44 mm, 1.52 mm or 1.77 mm.

FIGS. 9-22 show additional embodiments and features of exemplary staples discussed herein.

Exemplary Manufacturing Methods

The exemplary staples described herein may be manufactured in any suitable way. In at least one embodiment, a staple (e.g., staple 100 discussed herein) is produced from a solid piece of metal via a combination of wire EDM and grinding. In these embodiments (and others), the staple is a substantially uniform piece of material with each component or portion integrally connected.

In alternate embodiments, exemplary staples described herein may be produced by any other suitable manufacturing techniques, such as 3D printing.

Conclusion

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A staple comprising:
   a bridge with a substantially smooth top surface along a length of the bridge between a first end and a second end, wherein:
      the substantially smooth top surface comprises:
         a first edge and a second edge; and
         a constant width that is greater than a thickness of the bridge and a non-breaking surface between the first edge and second edge; and
      the substantially smooth surface transitions at each of the first end and the second end:
         to one of two outer leg surfaces; and
         downwardly to a face of one of two legs; and
   each of the two legs forming an angle of greater than approximately 20 degrees with the other leg.

2. The staple of claim 1, wherein each of the two legs comprises a proximal end and a distal end and each distal end includes a wedge-shaped tip.

3. The staple of claim 2, wherein each of the two legs comprises an inner surface in a particular plane and a plurality of teeth, wherein each of the plurality of teeth are cut out of a respective leg such that a point of each tooth lies substantially in the particular plane.

4. The staple of claim 3, wherein a midpoint of each of the two legs is located approximately at a midpoint of the width of the bridge.

5. The staple of claim 4, wherein the staple comprises at least one radius for transitioning the first edge and the second edge downwardly to the face of one of the two legs.

6. The staple of claim 5, wherein:
   each of a first subset of the plurality of teeth of a first leg of the two legs comprises a first angle; and
   each of a second subset of the plurality of teeth of the first leg comprises a second angle, wherein the second angle is less than the first angle.

7. The staple of claim 6, wherein the staple comprises nitinol.

8. The staple of claim 7, wherein:
   the length of the bridge is at least 8.00 mm; and
   a radius of the length of the bridge is at least 11.00 mm.

9. The staple of claim 8, wherein:
   the length of the bridge is at least 18.00 mm; and
   the radius of the length of the bridge is at least 31.00 mm.

10. The staple of claim 1, wherein the substantially smooth top surface comprises a constant radius between the first edge and the second edge.

11. A method of using a surgical staple, the method comprising:
    deforming a staple from a first position to a second position for inserting the staple into tissue of a patient, wherein:
       the staple comprises:
          a bridge with a substantially smooth top surface along a length of the bridge between a first end and a second end, wherein:
             the substantially smooth top surface comprises:
                a first edge and a second edge; and
                a constant width that is greater than a thickness of the bridge and a non-breaking surface between the first edge and second edge;
             the substantially smooth surface transitions at each of the first end and the second end:
                to one of two outer leg surfaces; and
                downwardly to a face of one of two legs; and
          in the first position, each of the two legs form an angle of greater than approximately 20 degrees with the other leg;
       in the second position, each of the two legs are substantially parallel with the other leg and strain is distributed substantially evenly throughout the bridge; and
       the staple, when inserted into the tissue of the patient exerts compressive force on the tissue of the patient.

12. The method of claim 11, wherein each of the two legs comprises a proximal end and a distal end and each distal end includes a wedge-shaped tip.

13. The method of claim 12, wherein:
    each of the two legs comprises an inner surface in a particular plane and a plurality of teeth; and
    each of the plurality of teeth are cut out of a respective leg such that a point of each tooth lies substantially in the particular plane.

14. The method of claim 13, wherein a midpoint of each of the two legs is located approximately at a midpoint of the width of the bridge.

15. The method of claim 14, wherein the staple comprises at least one radius for transitioning the first edge and the second edge downwardly to the face of one of the two legs.

16. The method of claim 15, wherein:
- each of a first subset of the plurality of teeth of a first leg of the two legs comprises a first angle; and
- each of a second subset of the plurality of teeth of the first leg comprises a second angle, wherein the second angle is less than the first angle.

17. The method of claim 16, wherein the staple comprises nitinol.

18. The method of claim 17, wherein:
- the length of the bridge is at least 8.00 mm; and
- a radius of the length of the bridge is at least 11.00 mm.

19. The method of claim 17, wherein:
- the length of the bridge is at least 18.00 mm; and
- a radius of the length of the bridge is at least 31.00 mm.

20. The method of claim 11, wherein the substantially smooth top surface comprises a constant radius between the first edge and the second edge.

* * * * *